United States Patent
Scheibel et al.

(10) Patent No.: US 8,030,024 B2
(45) Date of Patent: Oct. 4, 2011

(54) SYNTHESIS OF SPIDER DRAGLINE AND/OR FLAGELLIFORM PROTEINS

(75) Inventors: Thomas Scheibel, Munich (DE); Daniel Huemmerich, Mannheim (DE); Uri Gat, Jerusalem (IL)

(73) Assignee: Amsilk GmbH, Munich (DE)

( * ) Notice: Subject to any disclaimer, the term of this patent is extended or adjusted under 35 U.S.C. 154(b) by 1001 days.

(21) Appl. No.: 11/643,569

(22) Filed: Dec. 21, 2006

(65) Prior Publication Data

US 2008/0021553 A1    Jan. 24, 2008

Related U.S. Application Data

(63) Continuation of application No. PCT/EP2005/006905, filed on Jun. 27, 2005.

(60) Provisional application No. 60/583,227, filed on Jun. 25, 2004.

(51) Int. Cl.
*C12P 21/06* (2006.01)
*C07K 1/00* (2006.01)

(52) U.S. Cl. .......................... 435/69.1; 530/350

(58) Field of Classification Search .................. None
See application file for complete search history.

(56) References Cited

FOREIGN PATENT DOCUMENTS

WO    WO03/057727 A1    7/2003

OTHER PUBLICATIONS

Morais et al., Expression and characterization of recombinant human α-3/4-fucosyltransferase III from *Spodoptera frugiperda* (Sf9) and *Trichoplusia ni* (Tn) cells using the baculovirus expression system, Biochem. J., vol. 353, pp. 719-725.*
Growth and Maintenance of Insect cell Lines, User Manual from invitrogen, Jun. 8, 2009, pp. 1-30.*
Invitrogen: Growth and Maintenance of Insect cell Lines (Jun. 8, 2009), pp. 1-30.*
Summons (dated Jul. 27, 2009) to Attend Oral Proceedings in European Application No. 05766766.9.
Park et al., J. Biosci Bioeng, 87 (1999) 756-761.
Arcidiacono et al. Purification and characterization of recombinant spider silk expressed in *Escherichia coli*. *Applied Microbiology and Biotechnology*, vol. 49, (1998), pp. 31-38.
Gatesy et al. Extreme diversity, conservation, and convergence of spider silk fibroin sequences. *Science*, vol. 291, (2001), pp. 2603-2605.
Guerette et al. Silk properties determined by gland-specific expression of a spider fibroin gene family. *Science*, vol. 272, (1996), pp. 112-115.
Hinman et al. Synthetic spider silk: a modular fiber. *Tibtech*, vol. 18, (2000), pp. 374-379.
Huemmerich et al. Novel assembly properties of recombinant spider dragline silk proteins. *Current Biology*, vol. 14, (2004), pp. 2070-2074.
International Search Report corresponding to PCT application No. PCT/EP05/06905, Publication Date: Jan 12, 2006.
Knight et al. Liquid crystals and flow elongation in a spider's silk production line. *Proceedings of the Royal Society of London Series B*, vol. 266, (1999), pp. 519-523.
Lazaris et al. Spider silk fibers spun from soluble recombinant silk produced in mammalian cells. *Science*, vol. 295, (2002), pp. 472-476.
Li et al. The natural silk spinning process A nucleation-dependent aggregation mechanism? *European Journal of Biochemistry*, vol. 268, (2001), pp. 6600-6606.
Scheller et al. Production of spider silk proteins in tobacco and potato. *Nature Biotechnology*, vol. 19, (2001), pp. 573-577.
Shao et al. The effect of solvents on spider silk studied by mechanical testing and single-fibre Raman spectroscopy. *International Journal of Biological Macromolecules*, vol. 24, (1999), pp. 295-300.
Wong Po Foo et al. Genetic engineering of fibrous proteins: spider dragline silk and collagen. *Advanced Drug Delivery Reviews*, vol. 54, (2002), 1131-1143.
Yamao et al. Gene targeting in the silkworm by use of a baculovirus. *Genes and Development*, vol. 13, (1999), pp. 511-516.

\* cited by examiner

*Primary Examiner* — Alexander D Kim
(74) *Attorney, Agent, or Firm* — Baker & Daniels LLP

(57) ABSTRACT

The present invention is directed to a method of producing spider dragline and/or flagelliform proteins. The invention is further directed to a method of producing spider threads and to a dragline/flagelliform protein or dragline/flagelliform protein thread produced by these methods. The invention further provides the use of these proteins/threads in the field of biotechnology and/or medicine, in particular in the manufacture of wound closure or coverage systems, suture materials and in the manufacture of replacement materials, preferably artificial cartilage or tendon materials.

17 Claims, 4 Drawing Sheets

SEQUENCE LISTING

```
<160> NUMBER OF SEQ ID NOS: 8

<210> SEQ ID NO 1
<211> LENGTH: 1914
<212> TYPE: DNA
<213> ORGANISM: Araneus diadematus

<400> SEQUENCE: 1
gcacgagccg gatctggaca acaaggaccc ggacaacaag gacccggaca acaaggaccc      60
ggacaacaag gaccatatgg acccggtgca tccgccgcag cagcagccgc tggaggttat     120
ggacccggat ctggacaaca aggacccagc caacaaggac ctgccaaca aggacccggt     180
```

```
ggtcaaggac catatggacc cggtgcatcc gccgccgcag cagccgctgg tggatatgga      240
cccggttccg gacaacaagg accaggaggt caaggaccat atggacctgg ttcatccgct      300
gccgcagcag ccgctggagg taatggaccc ggatctggac aacaagggcc ggtcaacaa      360 ggtcctggac aacaaggacc cggtgcatcc gccgccgcag cagccgctgg aggatacgga      420
cccggatctg gacaacaagg acccggacaa caaggaccag gaggtcaagg accatatgga      480
cctggtgcat ccgccgctgc agcagccgct ggaggatacg gacccggatc tggacaacaa      540
ggacccggac aacaaggacc aggaggtcaa ggaccatatg acccggtgc atccgctgca      600 gcagcagccg ctggaggtta tggacccgga tctggacaac aaggacccgg acaacaagga      660
cctggacaac aaggacccgg tggtcaagga ccatatggac ccggtgcatc cgccgccgca      720
gcagccgctg gaggatacgg acccggttat ggacagcaag accaggaca caaggacca      780 ggaggtcaag gaccatatgg acctggtgca tccgccgcct cagcagcctc tggaggatac      840
ggacccggat ctggacaaca aggacccgga caacaaggac ctggaggtca aggaccatat      900
ggacctggtg catccgccgc agcagcagcc gctggaggtt atggacccgg atctggacaa      960
caaggaccag gccaacaagg acccggtcaa caaggacctg gacaacaagg acccggtggt     1020
caaggaccat atggacctgg tgcatccgcc gcagcagcag ccgctggagg ttatggaccc     1080
ggatctggac aacaaggacc cggtcaacaa ggacccggtc aacaaggacc cggtcaacaa     1140
ggacccggtc aacaaggacc ggccaacaa ggacccggtc aacaaggacc ggccaacaa      1200 ggacctggtc aacaaggtcc cggtggtcaa ggggcatatg gacctggtgc atccgccgca     1260
gcaggagccg ctggaggtta tggacccgga tctggacaac aaggacccgg acaacaagga     1320
cccggacaac aaggacccgg acaacaagga cccggacaac aaggacccgg acaacaagga     1380
cccggacaac aaggacccgg acaacaagga ccatatggac ctggtgcatc cgccgcagca     1440
gcagccgctg gaggttatgg acccggatct ggacaacaag acccggcca acaaggacct     1500 ggacaacaag acccgttgg tcaaggacca tatggacctg gtgcggcttc tgcagctgta     1560
tctgttggag atatggacc acaaagctcc tcggctcctg ttgcatcagc agccgcttct     1620 cgccttttctt ctccagcggc cagttctaga gtttcatcgg ctgtatcatc tttggtatct     1680
agtggaccta ctaatcaagc tgcactttct aatactatca gtagcgttgt atcgcaagtt     1740
agtgcaagta atcctggtct ttctggttgc gatgtacttg tgcaagcatt gctcgaagtt     1800
gtatcggccc tggtatctat ccttggatct tctagtatcg ggcaaattaa ctatggtgcc     1860
tctgctcagt acacccaaat ggtaggtcaa tctgtagctc aagcccttgc ttaa           1914
```

<210> SEQ ID NO 2  
<211> LENGTH: 1971  
<212> TYPE: DNA  
<213> ORGANISM: Araneus diadematus

<400> SEQUENCE: 2

```
gcaggatctt cagcagcagc ggccgcggca gcaagtggat ctggaggata cggacctgaa       60
aaccaaggac catctggacc tgtagcatat ggacctggtg acccgtatc ttcagctgca      120 gcagcagccg ctgcaggaag tggacctggt ggatacggac ctgaaaacca aggaccatct      180 ggaccggag atatggacc tggtggttcc ggatcttcag cagcagcagc agccgctgca       240
gcaagtggac ctggaggata tggacctgga agccaaggac catctggacc tggtggatcc      300
ggaggatatg gtcccggaag ccaagggcca tctggacctg gtgcatcttc ggcagcagca     360
gcagccgctg cagcaagtgg acctggagga tatggacctg gaagccaagg accatctgga     420
```

-continued

```
cctggagcat atggacctgg tgacccgga tcttcagctg cagcaagtgg acctggagga    480
tatggacctg gaagccaagg accatctgga cctggtggat ccggaggata tggtcccgga    540
agccaagggc catctggacc tggtgggcct ggtgcatctg cggcagcagc agcagccgct    600
gcagcaagtg gacctggagg atatggacct ggaagccaag gaccatctgg acctggagca    660
tatggacctg gtggacccgg atcttcagct gcagcaagtg gacctggagg atatggacct    720
ggaagccaag gaccatctgg acctggagca tatggacctg gtggacccgg atcttcagct    780
gcagcagcag ccgctgcagg aagtggacct ggtggatacg acctggaaa ccaaggacca    840
tctggacccg gaggatatgg acctggtggt cccggatctt cagcagcagc agccgctgca    900
gcaagtggac ctggaggata tggacctgga agccaaggac catctggacc tggagtatat    960
ggacctggtg gacccggatc ttcagctgca gcagcagccg ctgcaggaag tggacctggt   1020
ggatacggac ctggaaacca aggaccatct ggacccggag atatggacc tggtggttcc   1080
ggatcttcag cagcagcagc agccgctgca gcaagtggac ctggaggata tggacctgga   1140
agccaaggac catctggacc tggtggatcc ggaggatatg gtcccggaag ccaagggcca   1200
tctggacctg gtgcatcttc ggcagcagca gcagccgctg cagcaagtgg acctggagga   1260
tatggacctg gaagccaagg accatctgga cctggagcat atggacctgg tgacccgga    1320
tcttcagctg cagcaagtgg acctggagga tatggacctg gaagccaagg accatctggt   1380
cctggagcat atggacctgg tggacccgga tcttcagctg cagcagccgc tgcagcaagt   1440
ggacctggag gatatggacc tggaagccaa ggaccatctg gacctggtgg atcccgagga   1500
tatggtcccg gaagccaagg acctggtggg cctggagcat ctgcggcagc agcagcagcc   1560
gctgcagcaa gtggacctgg aggatatgga cctggaagcc aaggaccatc tggacctgga   1620
tatcaaggcc ctagtggtcc tggagcatat ggcccatctc cttctgcttc cgcatccgtt   1680
gcagcctctc gtttatcttc gcctgcagcc tcgtctagag tgtcttccgc tgtatcgtct   1740
ttagtgtcta gcggacctac gaatggtgct gctgtttctg gagctttgaa tagtttagta   1800
tctcagatta gtgcaagtaa tccaggttta tcgggatgtg atgctcttgt gcaggcatta   1860
ttggaattag tgtctgctct tgtggcaatt ctttcatctg caagtattgg ccaagtcaac   1920
gtcagctctg ttagtcagtc aactcaaatg attagccaag ctctttcata a             1971
```

<210> SEQ ID NO 3
<211> LENGTH: 636
<212> TYPE: PRT
<213> ORGANISM: Araneus diadematus

<400> SEQUENCE: 3

```
Ala Arg Ala Gly Ser Gly Gln Gln Gly Pro Gly Gln Gln Gly Pro Gly
1               5                   10                  15

Gln Gln Gly Pro Gly Gln Gln Gly Pro Tyr Gly Pro Gly Ala Ser Ala
            20                  25                  30

Ala Ala Ala Ala Ala Gly Gly Tyr Gly Pro Gly Ser Gly Gln Gln Gly
        35                  40                  45

Pro Ser Gln Gln Gly Pro Gly Gln Gln Gly Pro Gly Gly Gln Gly Pro
    50                  55                  60

Tyr Gly Pro Gly Ala Ser Ala Ala Ala Ala Ala Gly Gly Tyr Gly
65                  70                  75                  80

Pro Gly Ser Gly Gln Gln Gly Pro Gly Gly Gln Gly Pro Tyr Gly Pro
                85                  90                  95

Gly Ser Ser Ala Ala Ala Ala Ala Ala Gly Gly Asn Gly Pro Gly Ser
```

-continued

```
                100                 105                 110
Gly Gln Gln Gly Ala Gly Gln Gln Gly Pro Gly Gln Gln Gly Pro Gly
            115                 120                 125
Ala Ser Ala Ala Ala Ala Ala Ala Gly Gly Tyr Gly Pro Gly Ser Gly
            130                 135                 140
Gln Gln Gly Pro Gly Gln Gln Gly Pro Gly Gly Gln Gly Pro Tyr Gly
145                 150                 155                 160
Pro Gly Ala Ser Ala Ala Ala Ala Ala Gly Gly Tyr Gly Pro Gly
                165                 170                 175
Ser Gly Gln Gly Pro Gly Gln Gln Gly Pro Gly Gly Gln Gly Pro Tyr
            180                 185                 190
Gly Pro Gly Ala Ser Ala Ala Ala Ala Ala Gly Gly Tyr Gly Pro
            195                 200                 205
Gly Ser Gly Gln Gln Gly Pro Gly Gln Gln Gly Pro Gly Gln Gln Gly
            210                 215                 220
Pro Gly Gly Gln Gly Pro Tyr Gly Pro Gly Ala Ser Ala Ala Ala Ala
225                 230                 235                 240
Ala Ala Gly Gly Tyr Gly Pro Gly Tyr Gly Gln Gln Gly Pro Gly Gln
                245                 250                 255
Gln Gly Pro Gly Gly Gln Gly Pro Tyr Gly Pro Gly Ala Ser Ala Ala
            260                 265                 270
Ser Ala Ala Ser Gly Gly Tyr Gly Pro Gly Ser Gly Gln Gln Gly Pro
            275                 280                 285
Gly Gln Gln Gly Pro Gly Gln Gly Pro Tyr Gly Pro Gly Ala Ser
            290                 295                 300
Ala Ala Ala Ala Ala Ala Gly Gly Tyr Gly Pro Gly Ser Gly Gln Gln
305                 310                 315                 320
Gly Pro Gly Gln Gln Gly Pro Gly Gln Gln Gly Pro Gly Gln Gln Gly
                325                 330                 335
Pro Gly Gly Gln Gly Pro Tyr Gly Pro Gly Ala Ser Ala Ala Ala Ala
            340                 345                 350
Ala Ala Gly Gly Tyr Gly Pro Gly Ser Gly Gln Gln Gly Pro Gly Gln
            355                 360                 365
Gln Gly Pro Gly Gln Gln Gly Pro Gly Gln Gln Gly Pro Gly Gln Gln
            370                 375                 380
Gly Pro Gly Gln Gln Gly Pro Gly Gln Gln Gly Pro Gly Gln Gln Gly
385                 390                 395                 400
Pro Gly Gln Gln Gly Pro Gly Gln Gly Ala Tyr Gly Pro Gly Ala
                405                 410                 415
Ser Ala Ala Ala Gly Ala Ala Gly Gly Tyr Gly Pro Gly Ser Gly Gln
            420                 425                 430
Gln Gly Pro Gly Gln Gln Gly Pro Gly Gln Gln Gly Pro Gly Gln Gln
            435                 440                 445
Gly Pro Gly Gln Gln Gly Pro Gly Gln Gln Gly Pro Gly Gln Gln Gly
            450                 455                 460
Pro Gly Gln Gln Gly Pro Tyr Gly Pro Gly Ala Ser Ala Ala Ala Ala
465                 470                 475                 480
Ala Ala Gly Gly Tyr Gly Pro Gly Ser Gly Gln Gln Gly Pro Gly Gln
                485                 490                 495
Gln Gly Pro Gly Gln Gln Gly Pro Gly Gln Gln Gly Pro Tyr Gly Pro
            500                 505                 510
Gly Ala Ala Ser Ala Ala Val Ser Val Gly Gly Tyr Gly Pro Gln Ser
            515                 520                 525
```

Ser Ser Val Pro Val Ala Ser Val Ala Ser Arg Leu Ser Ser Pro
530                 535                 540

Ala Ala Ser Ser Arg Val Ser Ser Ala Val Ser Ser Leu Val Ser Ser
545                 550                 555                 560

Gly Pro Thr Lys His Ala Ala Leu Ser Asn Thr Ile Ser Ser Val Val
                565                 570                 575

Ser Gln Val Ser Ala Ser Asn Pro Gly Leu Ser Gly Cys Asp Val Leu
            580                 585                 590

Val Gln Ala Leu Leu Glu Val Val Ser Ala Leu Val Ser Ile Leu Gly
        595                 600                 605

Ser Ser Ser Ile Gly Gln Ile Asn Tyr Gly Ala Ser Ala Gln Tyr Thr
    610                 615                 620

Gln Met Val Gly Gln Ser Val Ala Gln Ala Leu Ala
625                 630                 635

<210> SEQ ID NO 4
<211> LENGTH: 410
<212> TYPE: PRT
<213> ORGANISM: Araneus diadematus

<400> SEQUENCE: 4

Ala Gly Ser Ser Ala Ala Ala Ala Ala Ser Gly Ser Gly Gly
1               5                   10                  15

Tyr Gly Pro Glu Asn Gln Gly Pro Ser Gly Pro Val Ala Tyr Gly Pro
                20                  25                  30

Gly Gly Pro Val Ser Ser Ala Ala Ala Ala Ala Ala Gly Ser Gly
            35                  40                  45

Pro Gly Gly Tyr Gly Pro Glu Asn Gln Gly Pro Ser Gly Pro Gly Gly
50                  55                  60

Tyr Gly Pro Gly Gly Ser Gly Ser Ser Ala Ala Ala Ala Ala Ala
65                  70                  75                  80

Ala Ser Gly Pro Gly Gly Tyr Gly Pro Gly Ser Gln Gly Pro Ser Gly
                85                  90                  95

Pro Gly Gly Ser Gly Gly Tyr Gly Pro Gly Ser Gln Gly Ala Ser Gly
            100                 105                 110

Pro Gly Gly Pro Gly Ala Ser Ala Ala Ala Ala Ala Ala Ala
            115                 120                 125

Ala Ser Gly Pro Gly Gly Tyr Gly Pro Gly Ser Gln Gly Pro Ser Gly
            130                 135                 140

Pro Gly Ala Tyr Gly Pro Gly Pro Gly Ser Ser Ala Ala Ala Ala
145                 150                 155                 160

Ala Ala Ala Ala Ser Gly Pro Gly Gly Tyr Gly Pro Gly Ser Gln Gly
                165                 170                 175

Pro Ser Gly Pro Gly Val Tyr Gly Pro Gly Gly Pro Gly Ser Ser Ala
            180                 185                 190

Ala Ala Ala Ala Ala Gly Ser Gly Pro Gly Gly Tyr Gly Pro Glu
        195                 200                 205

Asn Gln Gly Pro Ser Gly Pro Gly Gly Tyr Gly Pro Gly Gly Ser Gly
    210                 215                 220

Ser Ser Ala Ala Ala Ala Ala Ala Ala Ser Gly Pro Gly Gly Tyr
225                 230                 235                 240

Gly Pro Gly Ser Gln Gly Pro Ser Gly Pro Gly Gly Ser Gly Gly Tyr
                245                 250                 255

Gly Pro Gly Ser Gln Gly Gly Ser Gly Pro Gly Ala Ser Ala Ala Ala
            260                 265                 270

-continued

```
Ala Ala Ala Ala Ala Ser Gly Pro Gly Gly Tyr Gly Pro Gly Ser Gln
            275                 280                 285

Gly Pro Ser Gly Pro Gly Tyr Gln Gly Pro Ser Gly Pro Gly Ala Tyr
        290                 295                 300

Gly Pro Ser Pro Ser Ala Ser Ala Ser Val Ala Ala Ser Val Tyr Leu
305                 310                 315                 320

Arg Leu Gln Pro Arg Leu Glu Val Ser Ala Val Ser Ser Leu Val
                325                 330                 335

Ser Ser Gly Pro Thr Asn Gly Ala Ala Val Ser Gly Ala Leu Asn Ser
                340                 345                 350

Leu Val Ser Gln Ile Ser Ala Ser Asn Pro Gly Leu Ser Gly Cys Asp
            355                 360                 365

Ala Leu Val Gln Ala Leu Leu Glu Leu Val Ser Ala Leu Val Ala Ile
        370                 375                 380

Leu Ser Ser Ala Ser Ile Gly Gln Val Asn Val Ser Ser Val Ser Gln
385                 390                 395                 400

Ser Thr Gln Met Ile Ser Gln Ala Leu Ser
                405                 410
```

<210> SEQ ID NO 5
<211> LENGTH: 64
<212> TYPE: DNA
<213> ORGANISM: Artificial Sequence
<220> FEATURE:
<223> OTHER INFORMATION: Artificially synthesized oligonucleotide primer

<400> SEQUENCE: 5
ctagcccggg atgaaagaaa ccgctgctgc taaattcgaa cgccagcaca tggacagcgg    60
tcgg    64

<210> SEQ ID NO 6
<211> LENGTH: 64
<212> TYPE: DNA
<213> ORGANISM: Artificial Sequence
<220> FEATURE:
<223> OTHER INFORMATION: Artificially synthesized oligonucleotide primer

<400> SEQUENCE: 6
gatcccgacc gctgtccatg tgctggcgtt cgaatttagc agcagcggtt tctttcatcc    60
cggg    64

<210> SEQ ID NO 7
<211> LENGTH: 33
<212> TYPE: DNA
<213> ORGANISM: Artificial Sequence
<220> FEATURE:
<223> OTHER INFORMATION: Artificially synthesized oligonucleotide primer

<400> SEQUENCE: 7
ccttcccggt ccgccatgaa attcttagtc aac    33

<210> SEQ ID NO 8
<211> LENGTH: 31
<212> TYPE: DNA
<213> ORGANISM: Artificial Sequence
<220> FEATURE:
<223> OTHER INFORMATION: Artificially synthesized oligonucleotide primer

<400> SEQUENCE: 8
ccttcccgga ccgggcatag atgtaagaaa t    31

SYNTHESIS OF SPIDER DRAGLINE AND/OR FLAGELLIFORM PROTEINS

RELATED APPLICATIONS

This application is a continuation of PCT International Patent Application No. PCT/EP2005/006905, filed Jun. 27, 2005, which claims priority to U.S. Provisional Patent Application No. 60/583,227, filed Jun. 25, 2004, the disclosures of each of which are incorporated herein by reference in their entirety.

BACKGROUND

The present invention is directed to a method of producing spider dragline and/or flagelliform proteins. The invention is further directed to a method of producing spider threads and to a dragline/flagelliform protein or dragline/flagelliform protein thread produced by these methods. The invention further provides the use of these proteins/threads in the field of biotechnology and/or medicine, in particular in the manufacture of wound closure or coverage systems, suture materials and in the manufacture of replacement materials, preferably artificial cartilage or tendon materials, as well as in other commercial applications.

Spider dragline silk has extraordinary properties (1) originating in its composition as a semi crystalline polymer (2) that contains crystalline regions embedded in an amorphous matrix. X-ray diffraction and NMR show the crystalline regions to consist of pleated beta sheets of polyalanine stretches which are giving strength to the thread (3,4), while the predominant secondary structure of the amorphous matrix is a glycine rich $3_1$ helix providing elasticity (5). Freshly secreted silk proteins are stored at high concentrations (6) as a liquid crystalline dope (7,8) that is altered by changes in ionic composition, pH (from pH 6.9 to 6.3) (9,10) and water extraction (10,11) during its passage through the spinning duct to be finally converted into a solid thread induced by extensional flow (12).

All dragline silks studied so far consist of at least two different proteins with molecular masses of up to several hundred kDa (13). The individual contribution of the two major dragline silk proteins of *Araneus diadematus*, ADF-3 and ADF-4, to dragline thread assembly and structure has not been determined so far. Analyzing the primary structures revealed that ADF-3 and ADF-4 (14,15) have similar proline contents and polyalanine motifs, but they differ in glutamine and serine content as well as in length of the glycine-rich regions. Importantly, the properties of silk threads cannot be inferred from the underlying protein sequences. Although the quality of a silk thread is based on the primary structure of the involved proteins, it further depends on the silk assembly process (8), which necessitates experimental analysis of structural and assembly properties.

Scientific and commercial interest initiated the investigation of industrial scale manufacturing of spider silk. Native spider silk production is impractical due to the cannibalism of spiders, and artificial production has encountered problems in achieving both sufficient protein yield and quality thread-assembly. Bacterial expression yielded low protein levels (16), likely caused by a different codon usage in bacteria and in spiders. Synthetic genes with a codon usage adapted to the expression host led to higher yields (13,17), but the proteins synthesized thereof showed different characteristics in comparison to native spider silks. Expression of partial dragline silk cDNAs in mammalian cell lines did yield silk proteins (e.g. ADF-3) that could be artificially spun into 'silken' threads, albeit as yet of inferior quality (18).

WO03060099 relates to methods and devices for spinning biofilament proteins into fibers. This invention is particularly useful for spinning recombinant silk proteins from aqueous solutions and enhancing the strength of the fibers and practicality of manufacture such as to render commercial production and use of such fibers practicable. Therein, it is disclosed to express spider silk proteins in mammalian cells, e.g. transgenic goat mammary gland cells.

SUMMARY

Therefore, it is an object of the present invention to provide an improved method for the manufacture of spider silk proteins in high yield and superior quality. It is a further object to provide an improved expression system to be used in said method. Additional objects are to simplify the manufacturing process for spider silk proteins/threads and the provision of new proteins/threads and further materials based on spider silk proteins for use in biotechnology and medicine.

These objects are solved by the subject-matter of the independent claims. Preferred embodiments are set forth in the dependent claims.

Regarding the drawbacks of the prior art methods, which are related to the production of spider silk proteins and threads derived therefrom, a different and more efficient route to synthesize authentic spider silk proteins was achieved by the inventors.

Spider dragline silk, which exhibits extraordinary strength and toughness, is primarily composed of two related proteins whose role in thread assembly and whose contribution to the mechanical properties of dragline threads is largely unknown.

In order to elucidate this role, a baculovirus expression system was used by the inventors to produce recombinant ADF-3 and ADF-4, the two major dragline silk proteins of the garden spider *Araneus diadematus*, in host insect cells. It was shown that ADF-4, but not ADF-3 readily self-assembled into filaments in the cytosol of the cells. These ADF-4 filaments displayed the exceptional chemical stability typical for authentic spider dragline silk threads. As a result, the properties of ADF-4 show its role as the structural key player in dragline silk.

Thus far, little is known about the structure, function and possible interplay between the two major protein components of spider dragline silk threads. The inventors observed that, despite their similarities in primary structure, ADF-3 and ADF-4 display surprisingly different properties. Whilst, ADF-3 represents an intrinsically soluble protein, ADF-4 is virtually insoluble under the experimental conditions employed and forms filamentous aggregates in the cytoplasm of Sf9 cells with a chemical stability comparable to natural dragline threads. The similarities between ADF-4 filaments and native dragline silk threads suggest that ADF-4 is the structural 'key player' in dragline threads providing its chemical and physical strength. Since thread formation has to be fast at natural reeling speeds of 1-10 cm/s (19), an easily assembling compound, such as ADF-4, is mandatory for silk formation. However, the tendency of ADF-4 to aggregate implies that other factors within the spinning dope are likely required to keep it from premature polymerization in the gland. These factors are likely to be post-translational modifications such as phosphorylation and glycosylation. Additionally, ADF-4's solubility could be influenced by proteins that are co-secreted and also stored in the dope. Although ADF-3 did not influence solubility of ADF-4 within the cytosol of the insect cells, it may still play an important role in regulating ADF-4 solubility during or after secretion from the spider gland. The specific conditions present in the secretory pathway of the spider gland cells as well as in the glands' lumen may lead to interactions between ADF-3 and ADF-4, which regulates silk thread assembly.

Spider silks can be regarded as the benchmarks for future polymer design not only due to their superb quality but are also preferred since they could be produced economically and in an environment-friendly way from aqueous solvents under ambient temperatures and pressures. However, major barriers remain our ability to match the native silk fiber production process. The inventors hereby provide an ideal system for large-scale production of spider silk proteins. Further, the results provided herein constitute the essential basis for elucidating the function and interplay of the two major components of spider silk dragline proteins, e.g. of *Araneus* dragline silk, ADF-3 and ADF-4. Such knowledge is essential for spinning silk threads from recombinant proteins and for production of a new generation of fibrous materials.

Therefore, the present invention provides according to a first aspect, a method of producing spider silk dragline proteins derived from the major ampullate gland and/or proteins derived from the flagelliform gland, comprising the following steps:
 a) providing a nucleic acid sequence coding for one or more spider dragline and/or flagelliform proteins,
 b) introducing the nucleic acid sequence(s) provided in a) into an insect cell,
 c) expressing the dragline and/or flagelliform proteins; and
 d) recovering said dragline and/or flagelliform proteins.

Thus, as mentioned above, one of the major advantages offered by the method of the present invention resides in the provision of a novel expression system for spider silk dragline proteins, i.e. the expression in insect cells. It surprisingly turned out that, as explained above, the expression of those proteins in insect cells is superior to the expression in other cells, as, for example, bacterial cells and mammalian cells. This improvement equally affects the quality, i.e. mechanical properties and the like, as well as the yield of spider silk dragline proteins, which can be obtained by the method of the present invention.

As an example, according to the method of ref. 16, 4 mg/l of cells were obtained, which could not be spun into threads; in ref. 18, 25 mg/l of cells (threads were obtained, however, had poor quality). In the present invention, >30 mg/l of cells could be obtained (self-assembling, stabile thread).

The dragline/flagelliform proteins encoded by the nucleic acid sequence provided in step a) of the above method are preferably selected from dragline and/or flagelliform proteins of orb-web spiders (Araneidae).

More preferably, the dragline proteins and/or flagelliform proteins are derived from one or more of the following spiders: *Arachnura higginsi, Araneus circulissparsus, Araneus diadematus, Argiope picta,* Banded Garden Spider (*Argiope trifasciata*), Batik Golden Web Spider (*Nephila antipodiana*), Beccari's Tent Spider (*Cyrtophora beccarii*), Bird-dropping Spider (*Celaenia excavata*), Black-and-White Spiny Spider (*Gasteracantha kuhlii*), Black-and-yellow Garden Spider (*Argiope aurantia*), Bolas Spider (*Ordgarius furcatus*), Bolas Spiders—Magnificent Spider (*Ordgarius magnificus*), Brown Sailor Spider (*Neoscona nautica*), Brown-Legged Spider (*Neoscona rufofemorata*), Capped Black-Headed Spider (*Zygiella calyptrata*), Common Garden Spider (*Parawixia dehaani*), Common Orb Weaver (*Neoscona oxancensis*), Crab-like Spiny Orb Weaver (*Gasteracantha cancriformis (elipsoides)*), Curved Spiny Spider (*Gasteracantha arcuata*), *Cyrtophora moluccensis, Cyrtophora parnasia, Dolophones conifera, Dolophones turrigera,* Doria's Spiny Spider (*Gasteracantha doriae*), Double-Spotted Spiny Spider (*Gasteracantha mammosa*), Double-Tailed Tent Spider (*Cyrtophora exanthematica*), *Aculeperia ceropegia, Eriophora pustulosa,* Flat Anepsion (*Anepsion depressium*), Four-spined Jewel Spider (*Gasteracantha quadrispinosa*), Garden Orb Web Spider (*Eriophora transmarina*), Giant Lichen Orbweaver (*Araneus bicentenarius*), Golden Web Spider (*Nephila maculata*), Hasselt's Spiny Spider (*Gasteracantha hasseltii*), *Tegenaria atrica, Heurodes turrita,* Island Cyclosa Spider (*Cyclosa insulana*), Jewel or Spiny Spider (*Astracantha minax*), Kidney Garden Spider (*Araneus mitificus*), Laglaise's Garden Spider (*Eriovixia laglaisei*), Long-Bellied Cyclosa Spider (*Cyclosa bifida*), Malabar Spider (*Nephilengys malabarensis*), Multi-Coloured St Andrew's Cross Spider (*Argiope versicolor*), Ornamental Tree-Trunk Spider (*Herennia ornatissima*), Oval St. Andrew's Cross Spider (*Argiope aemula*), Red Tent Spider (*Cyrtophora unicolor*), Russian Tent Spider (*Cyrtophora hirta*), Saint Andrew's Cross Spider (*Argiope keyserlingi*), Scarlet Acusilas (*Acusilas coccineus*), Silver Argiope (*Argiope argentata*), Spinybacked Orbweaver (*Gasteracantha cancriformis*), Spotted Orbweaver (*Neoscona domiciliorum*), St. Andrews Cross (*Argiope aetheria*), St. Andrew's Cross Spider (*Argiope Keyserlingi*), Tree-Stump Spider (*Poltys illepidus*), Triangular Spider (*Arkys clavatus*), Triangular Spider (*Arkys lancearius*), Two-spined Spider (*Poecilopachys australasia*), *Nephila* species, e.g. *Nephila clavipes, Nephila senegalensis, Nephila madagascariensis* and many more (for further spider species, see also below). *Araneus diadematus* is most preferred.

According to one preferred embodiment, the dragline proteins produced by the method of the present invention are the dragline proteins are wild type ADF-3, ADF-4, MaSp I, MaSp II and the flagelliform protein is FLAG. The term ADF-3/-4 is used in the context of MaSp proteins produced by *Araneus diadematus* (*Araneus diadematus* fibroin-3/-4). Both proteins, ADF-3 and 4 belong to the class of MaSp II proteins (major ampullate spidroin II).

In a further embodiment, the nucleic acid sequence provided in step a) is ADF-3 (SEQ ID NO:1) and/or ADF-4 (SEQ ID NO:2), or a variant thereof.

It is noted that two different kinds of ADF-3 and ADF-4 coding sequences are contemplated in this invention: first, the already published sequence of ADF-3 and ADF-4 (herein: "wild type" sequence) and, second, a variant thereof, encoded by SEQ ID NO: 1 (ADF-3) and 2 (ADF-4). The wild type sequences were already published and are available under the accession numbers U47855 and U47856 (SEQ ID NO: 3 and 4).

As explained above, the silk fiber has crystalline regions of β-sheets interspersed with elastic amorphous segments similar to liquid crystalline polymers. These two segments are represented by two different proteins, MaSp I (major ampullate spidroin I) and MaSp II (major ampullate spidroin II) coded by different genes.

The nucleic acid sequence provided in step a) of the method of the present invention is preferably ADF-3, ADF-4 (SEQ ID NO: 1 and 2) or a variant thereof. SEQ ID NO: 3 and 4 are showing the corresponding amino acid sequences of the wild type sequences.

Further spider silk proteins, which can preferably be produced by the method of the present invention (i.e. alone or in combination with further proteins) and their database accession numbers are:

spidroin 2 *[Araneus bicentenarius]*gi|2911272
major ampullate gland dragline silk protein-1 *[Araneus ventricosus]*gi|27228957
major ampullate gland dragline silk protein-2 *[Araneus ventricosus]*gi|27228959 ampullate spidroin 1 *[Nephila madagascariensis]*gi|13562006
major ampullate spidroin 1 *[Nephila senegalensis]* gi|13562010
major ampullate spidroin 1 *[Latrodectus geometricus]* gi|13561998
major ampullate spidroin 1 *[Argiope trifasciata]*gi|13561984
major ampullate spidroin 1 *[Argiope aurantia]*gi|13561976
dragline silk protein spidroin 2 *[Nephila clavata]* gi|16974791
major ampullate spidroin 2 *[Nephila senegalensis]* gi|13562012
major ampullate spidroin 2 *[Nephila madagascariensis]* gi|13562008
major ampullate spidroin 2 *[Latrodectus geometricus]* gi|13562002

The invention also encompasses a spider dragline protein, which is encoded by the nucleic acid sequence of SEQ ID NO. 1 or 2, or variants of those nucleic acid sequences. These variants are each defined as having one or more substitutions, insertions and/or deletions as compared to the sequence of SEQ ID NO. 1 or 2, provided that said variants hybridize under moderately stringent conditions to a nucleic acid which comprises the sequence of SEQ ID NO. 1 or 2, or provided that said variants comprise nucleic acid changes due to the degeneracy of the genetic code, which code for the same or a functionally equivalent amino acid as the nucleic acid sequence of SEQ ID NO. 1 or 2.

The term "nucleic acid sequence" refers to a heteropolymer of nucleotides or the sequence of these nucleotides. The terms "nucleic acid" and "polynucleotide" are used interchangeably herein to refer to a heteropolymer of nucleotides.

Stringency of hybridization, as used herein, refers to conditions under which polynucleotide duplexes are stable. As known to those of skill in the art, the stability of duplex is a function of sodium ion concentration and temperature (see, for example, Sambrook et al., Molecular Cloning: A Laboratory Manual $2^{nd}$ Ed. (Cold Spring Harbor Laboratory, (1989)). Stringency levels used to hybridize can be readily varied by those of skill in the art.

As used herein, the phrase "moderately stringent conditions" refers to conditions that permit DNA to bind a complementary nucleic acid that has about 60% identity, preferably about 75% identity, more preferably about 85% identity to the DNA; with greater than about 90% identity to said DNA being especially preferred. Preferably, moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 65° C.

According to a preferred embodiment, the method of the present invention provides spider silk proteins consisting of a polymer, the building blocks thereof being defined as one or more of the proteins as defined above or a variant of said proteins. The amino acid sequences of the proteins of the present invention also encompass all sequences differing from the herein disclosed sequences by amino acid insertions, deletions, and substitutions.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Insertions" or "deletions" are typically in the range of about 1 to 5 amino acids, preferably about 1, 2 or 3 amino acids. Amino acid additions typically are not more than 100, preferably not more than 80, more preferably not more than 50, most preferred not more than 20 amino acids, which are added on and/or inserted into the proteins of the present invention. It is noted that only those additions are contemplated in this invention, which do not negatively affect the mechanical and further characteristics of the proteins disclosed herein.

The variation allowed may be experimentally determined by systematically making insertions, deletions, or substitutions of amino acids in a protein using recombinant DNA techniques and assaying the resulting recombinant variants for activity. This does not require more than routine experiments for the skilled artisan.

According to a preferred embodiment, one or more of the nucleic acid sequences defined above are contained in a vector. Preferably, this vector is an expression vector, which comprises the nucleic acid sequence coding for one or more dragline proteins and/or flagelliform proteins as defined above and one or more regulatory sequences. Such regulatory sequences may preferably comprise promoters p10 and/or polyhedrin, but other late and very late baculoviral promoters can be used as well.

The vector is more preferably a viral vector, most preferably a baculovirus vector system or a vaccinia virus vector system. Further viral vector systems may also be used in this invention. From case to case, a modification of the vector may be needed. Examples for further viral vectors are adenoviruses and all negative-strand RNA-viruses, e.g. rabies, measles, RSV, etc.

As insect cells, *Lepidoptera* insect cells may preferably be used, more preferably cells from *Spodoptera frugiperda* and from *Trichoplusia ni*. Most preferably, the insect cell is a Sf9, Sf21 or high five cell.

One advantage of insect cell expression system, for example regarding bacterial systems, resides in the fact that the proteins produced are glycosylated, thereby being a target for degradation by microorganisms. This characteristic may be of importance, for example, in the field of medicine, whenever the silk proteins are intended for an in vivo use, in which biological degradation is desired. This characteristic may in particular find application in suture materials and wound closure and coverage systems.

According to a further preferred embodiment, the only dragline protein expressed is wild type ADF-4 or ADF-4 encoded by SEQ ID NO: 2.

The inventors surprisingly found out that, in contrast to the conviction of the prior art, only one of the two known major dragline proteins is needed for the manufacture and assembly of a dragline silk thread. Therefore, the already known approaches for the manufacture of dragline silks can be considerably simplified by using only one component for preparing the dragline silk instead of two, as it is known in the art.

Class MaSp I can be distinguished from MaSp II by the content of amino acid proline. Within the class of MaSp II, no further official subranges are existing. However, ADF-3 and ADF-4 are differing from each other by their content of amino acid glutamine and in the spacing and length of the polyalanine regions. Therefore, one of skill in the art can easily determine those regions in MaSp II, which are corresponding to ADF-3 and ADF-4, respectively.

Preferably, the expression of said dragline and/or flagelliform proteins occurs by secretory expression. For further explanation, see chapter Examples. Alternatively, the expression occurs by cytoplasmatical production. As it is shown in the Examples, the conditions, which are present in the insect cells used for expression led to the surprising result that—as mentioned above—spider silk proteins were expressed in high yield an good quality and, moreover, a self-assembly of those proteins to threads occurred already in the cytoplasm without any further production step.

In a second aspect, the present invention provides a method for producing spider dragline and flagelliform protein threads, comprising the following steps:
 a) expressing spider dragline proteins and/or flagelliform proteins as defined above,
 b) recovering said proteins, and
 c) spinning said proteins into threads by a suitable method.

In step c), spinning methods may be used, which are per se known in the art. For example, a dope solution of spider silk protein is extruded through a spinneret to form a biofilament. The resulting biofilament can be drawn or stretched. Whenever both crystalline and amorphous arrangements of molecules exist in biofilaments, drawing or stretching will apply shear stress sufficient to orient the molecules to make them more parallel to the walls of the filament and increase the tensile strength and toughness of the biofilament.

The dope solution may contain a mixture of silk proteins from one or more spider species, or silk proteins from different silk-producing genera, for example, a mixture of silk proteins from spiders and *B. mori*. In the most preferred embodiments, the silk proteins are dragline and/or flagelliform silks from *N. clavipes* or *A. diadematus*, particularly the proteins MaSpI, MaSpII, ADF-3, and ADF-4. In alternate embodiments, the dope solution contains a mixture of silk proteins and one or more synthetic polymers or natural or synthetic biofilament proteins.

Preferably, the dope solution is at least 1%, 5%, 10%, 15% weight/volume (w/v) silk protein. More preferably, the dope solution is as much as 20%, 25%, 30%, 35%, 40%, 45%, or 50% w/v silk protein. In preferred embodiments, the dope solution contains substantially pure spider silk protein. In preferred embodiments, the dope has a pH of approximately 6.9.

By "dope solution" is meant any liquid mixture that contains silk protein and is amenable to extrusion for the formation of a biofilament or film casting. Dope solutions may also contain, in addition to protein monomers, higher order aggregates including, for example, dimers, trimers, and tetramers. Normally, dope solutions are aqueous solutions of pH 4.0-12.0 and having less than 40% organics or chaotropic agents (w/v). Preferably, the dope solutions do not contain any organic solvents or chaotropic agents, yet may include additives to enhance preservation, stability, or workability of the solution.

By "filament" is meant a fiber of indefinite length, ranging from microscopic length to lengths of a mile or greater. Silk is a natural filament, while nylon and polyester as an example are synthetic filaments.

By "biofilament" is meant a filament created (e.g., spun) from a protein, including recombinantly produced spider silk protein.

Further information regarding how to spin spider silk protein fibers may be found in WO03060099 (Karatzas et al.), published Jul. 24, 2003, which is incorporated herein by reference.

According to a third aspect, a spider dragline protein or flagelliform protein/thread is provided, which is obtainable by the methods as defined herein.

The invention further encompasses a spider dragline protein or thread, comprising an amino acid sequence encoded by the nucleic acid of SEQ ID NO: 1 and/or 2; or a variant thereof.

In a preferred embodiment, the spider dragline protein/thread only comprises wild type ADF-4 or an amino acid encoded by the nucleic acid of SEQ ID NO: 2 as a dragline protein.

A vector, which comprises a nucleic acid coding for wild-type ADF-4 as only dragline protein or which comprises the nucleic acid of SEQ ID NO: 1 and/or SEQ ID NO: 2 is provided in the present invention as a fourth aspect.

In a fifth aspect, a baculovirus vector is provided, which comprises a nucleic acid coding for one or more dragline and/or flagelliform proteins, preferably for the dragline proteins ADF-3, ADF-4 (wild type) and/or for the flagelliform protein FLAG, ADF-3 (SEQ ID NO:1) and/or ADF-4 (SEQ ID NO:2).

As already explained above, the proteins/threads as defined herein may be used in the field of biotechnology and/or medicine, preferably for the manufacture of wound closure or coverage systems, suture materials for use in neurosurgery or ophthalmic surgery.

Furthermore, the proteins/threads may preferably be used for the manufacture of replacement materials, preferably artificial cartilage or tendon materials.

Additionally, the threads/fibers of the invention can be used in the manufacture of medical devices such as medical adhesive strips, skin grafts, replacement ligaments, and surgical mesh; and in a wide range of industrial and commercial products, such as clothing fabric, bullet-proof vest lining, container fabric, bag or purse straps, cable, rope, adhesive binding material, non-adhesive binding material, strapping material, vehicle covers and parts, construction material, weatherproofing material, flexible partition material, sports equipment; and, in fact, in nearly any use of fiber or fabric for which high tensile strength and elasticity are desired characteristics. Adaptability and use of the stable fiber product in other forms, such as a dry spray coating, bead-like particles, or use in a mixture with other compositions is also contemplated by the present invention.

Unless otherwise defined, all technical and scientific terms used herein have the same meaning as commonly understood by one of ordinary skill in the art to which this invention pertains. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention is now further illustrated by Examples and the accompanying drawings, which are showing the following:

DETAILED DESCRIPTION

EXAMPLES

The improvement provided herein was based on the idea to express and study the two major protein constituents of *Araneus diadematus* dragline silk simultaneously. Since insects belong to the same phylum as spiders, the inventors chose the insect cell line Sf9 (derived from the fall armyworm *Spodoptera frugiperda*), for the expression of adf-3 and adf-4 using baculoviruses as vectors. Recombinant baculoviruses were generated containing partial cDNAs of adf-3 and adf-4 (14). In order to monitor synthesis, both proteins were provided with a His$_6$-Tag. To exclude artificial influences caused by the tag, versions without His$_6$-Tag were also employed.

The recombinant viruses were used to infect Sf9 cells for production of the spider silk proteins in the cytoplasm. After 3 days of incubation, infected cells were lyzed by sonification and insoluble cell contents were separated from soluble material by sedimentation. The sediment was dissolved in guanidinium thiocyanate (GdmSCN) prior to analysis by immunoblotting.

Figure 1:
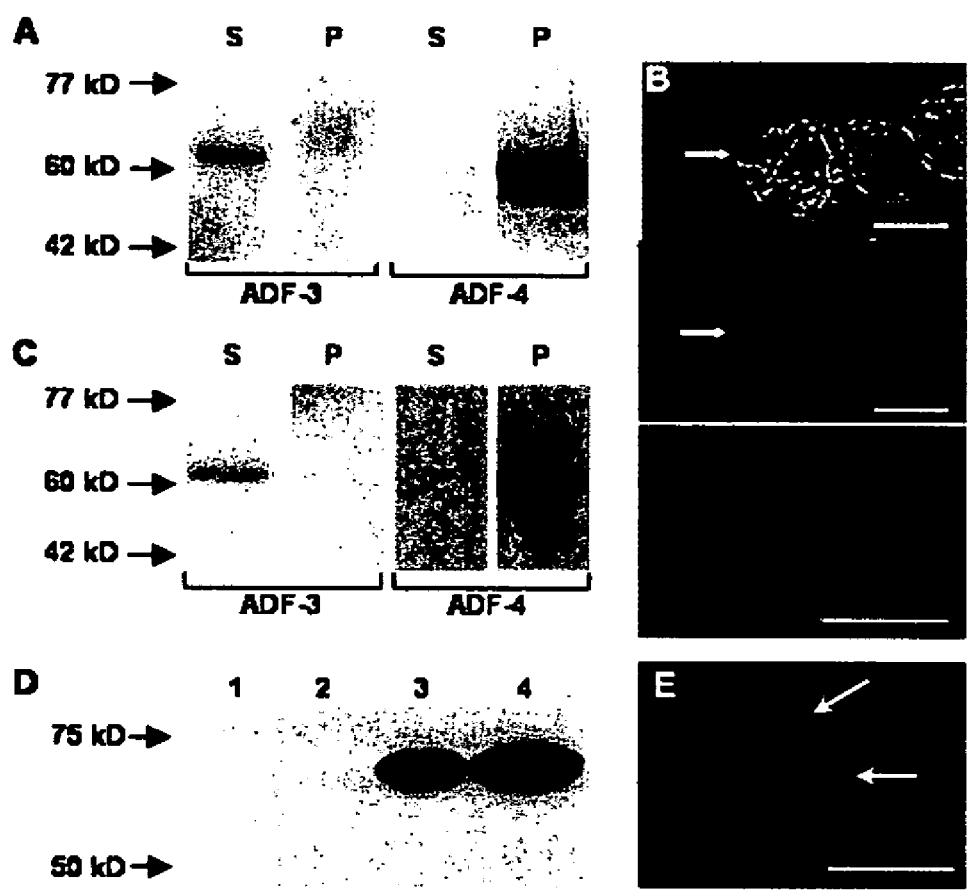
FIG. 1 Expression of adf-3 and adf-4 in Sf9 cells. (A) Solubility of ADF-3 and ADF-4 after synthesis. Soluble (S) and insoluble components (P) of cell lysates were separated by sedimentation. Proteins were detected by immunoblotting with an anti-His$_6$ antibody. (B) Filament in adf-4 expressing cell, as seen with light microscopy (upper panel) and with fluorescence microscopy after immunocytochemistry (middle panel). An additional confocal fluorescence image after immunocytochemistry of another cell is shown in the lower panel. Scale bars: 10 µm. (C) Solubility of co-synthesized ADF-3 and ADF-4. Soluble (S) were separated from insoluble (P) cell components by sedimentation. ADF-3 was detected with S-protein-peroxidase conjugates after western blotting and ADF-4 with anti-T7-tag antibodies. (D) Sf9 cells in suspension were infected with the mel-His$_6$-adf-4 virus. At the indicated times (in days post infection) aliquots equivalent to $6 \times 10^4$ cells were taken from the culture media, centrifuged to remove cells and subjected to SDS-PAGE followed by immunoblotting. (E) Cells infected for 3 days with the mel-his$_6$-adf-4 virus were subjected to immunofluorescence. Secretion vesicles on the cell surface could be clearly detected. Scale bar 10 µm.
Figure 4:
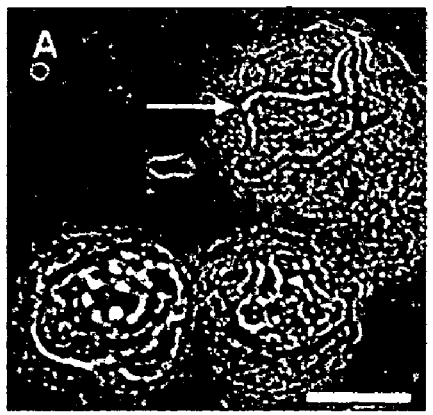
FIG. 4 (A) Filaments of ADF-4 without His$_6$-tag formed within Sf9 cells were visualized by light microscopy. (B) The morphology of filaments obtained after dual expression of adf-3 and adf-4 was investigated by scanning electron microscopy. (C) adf-3 expressing Sf9 cell were imaged by light microscopy. (D) Cellular localization of ADF-3. Cells infected for 3 days with adf-3 viruses were subjected to immunofluorescence analysis. (E) ADF-4 aggregates formed after renaturation in vitro visualized by scanning electron microscopy. (F) Chemical stability of ADF-4 aggregates formed in vitro. After treatment with denaturants, as indicated, solubilized ADF-3 was detected by immunoblotting. Scale bars 5 µm (B,E) and 10 µm (A,C,D).
Figure 4:
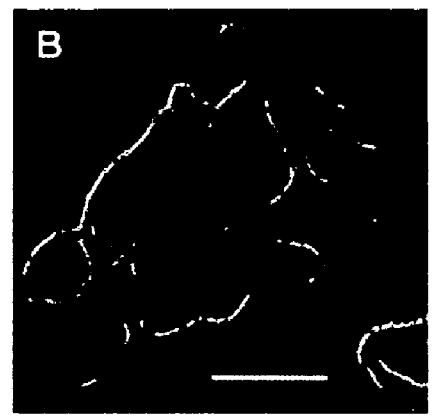
Figure 4:
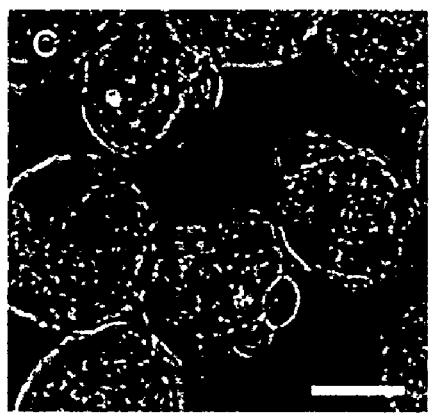
Figure 4:
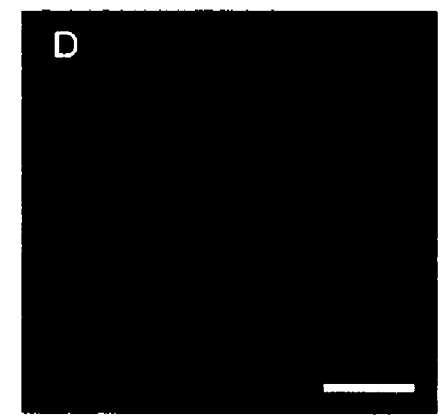
Figure 4:
Figure 4:
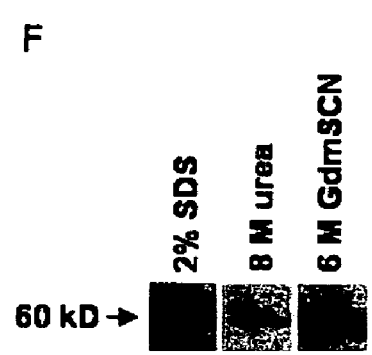

While a large fraction of ADF-3 was found to be soluble, ADF-4 was almost entirely insoluble three days after infection under the conditions employed (FIG. 1A) and independent from the presence of the His$_6$-Tag (FIG. 4A). Surprisingly, investigating the aggregates in adf-4 expressing cells revealed filaments that coiled throughout the cytoplasm, whereby most of the cells contained only one or few filaments of a uniform width (FIG. 1B). In contrast, cells infected with control viruses or the adf-3 encoding virus never produced such filaments (FIG. 4C, D). Immunofluorescence performed on the infected cells using anti-His$_6$ antibodies showed specific staining of the filaments thus confirming that the filaments were composed of ADF-4 (FIG. 1B).

Next, the inventors investigated whether ADF-3 and ADF-4 can co-assemble into filaments. The inventors generated a recombinant baculovirus containing both adf-3 and adf-4 under different and independent promoters, using the pFastbacDUAL donor plasmid. Infection of Sf9 cells with this virus resulted in synthesis of both proteins and the formation of protein filaments that showed similar appearance in comparison to the filaments formed by synthesis of ADF-4 alone (FIG. 4B). Interestingly, filaments assembled in the DUAL expression system were entirely formed by ADF-4 with no incorporated or stably associated ADF-3 (FIG. 1C and data not shown).

In order to study whether the apparent self-assembly is solely based on properties of ADF-4 or whether additional factors or modifications are involved, the inventors created a recombinant baculovirus coding for a secreted form of His$_6$-ADF-4. Infection of cells with this virus led to accumulation of ADF-4 in the culture media of the cells (FIG. 1D). Immunofluorescence revealed the abundance of ADF-4 containing secretory vesicles at the cell surface of the infected cells (FIG. 1E). Strikingly, the inventors did not observe any formation of ADF-4 filaments neither in compartments of the host cells nor in the culture media.

Silk thread formation generally depends on the protein concentration as well as on additional factors. Interestingly the intracellular pH 6.3 of Sf9 cells corresponds to the pH in the spinning dope prior to silk thread assembly (19). Further factors required for ADF-4 filament assembly in the cytosolic environment remain elusive. Investigating the self-assembling properties of ADF-4 in vitro stressed the importance of additional factors. Soluble ADF-4 was readily obtained by dissolving filaments in 6 M GdmSCN. Dissolved ADF-4 rapidly aggregated upon removal of GdmSCN by dialysis or dilution.

However, the ADF-4 aggregates formed in vitro showed neither fibrillar structures nor did they display the chemical stability of ADF-4 filaments formed inside the Sf9 cells (see below and FIG. 4E, F). The above findings indicate the importance of the specific cytosolic environment, which may include additional, so far unresolved, cytoplasmatic factors important for controlled self-assembly.

Figure 2:
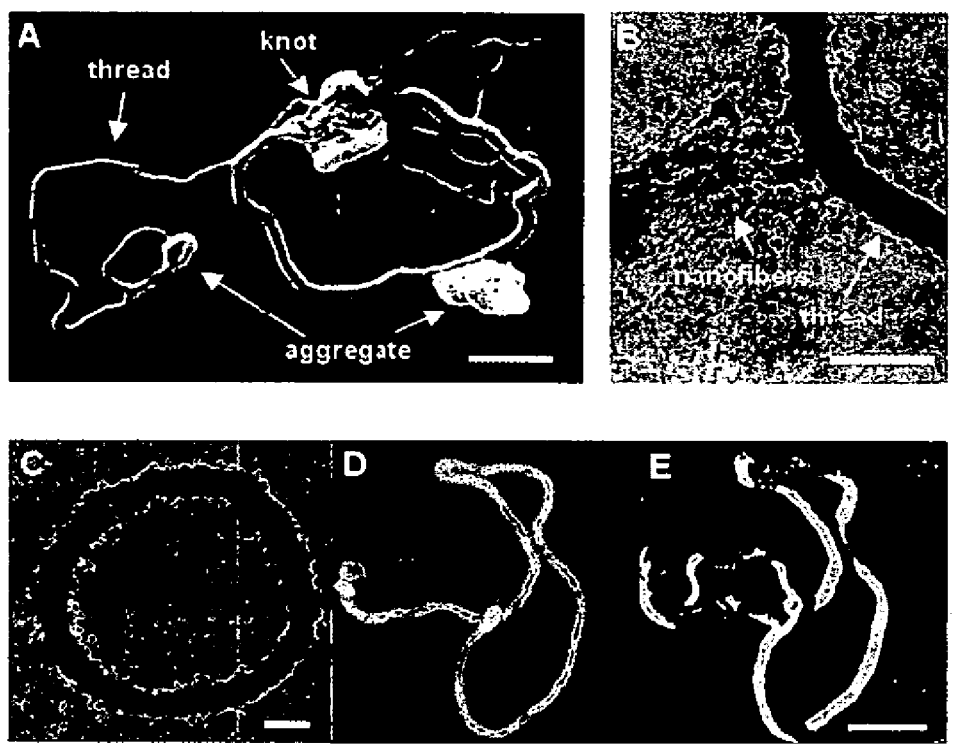
FIG. 2 Morphology of ADF-4 filaments and aggregates. (A) Scanning electron microscopy on purified filaments. Scale bar: 5 µm (B) Transmission electron microscopy on purified filaments. Scale bar: 500 nm (C) Immunoelectron microscopy on purified filaments using mouse anti-His$_6$ antibodies followed by gold-conjugated anti-mouse antibodies. Scale bar: 500 nm (D, E) Atomic force microscopy (AFM): (D) height image (E) deflection image. The height of the filament is 0.7 µm. Scale bar 5 µm.

Next the inventors characterized the morphology of ADF-4 filaments. The diameters of filaments ranged from 200 nm to 1 µm, however for each single filament the diameter was found to be constant. Furthermore, the filaments showed lengths up to 100 µm and often terminated in knots, branches or formed closed circles (FIG. 2A, D, E). Filaments displayed a smooth surface and were often associated with nanofibers (diameter~5 nm) and other protein aggregates (FIG. 2). Immunoblotting, and immunoelectron microscopy indicated that filaments and associated assembly forms were composed of ADF-4 (FIG. 2C, 3A). Besides ADF-4 no other abundant protein could be detected in filaments as visualized by SDS-PAGE analysis followed by silver staining (FIG. 3A). The low number of filaments per cell and the recruitment of almost the entire cellular ADF-4 into the aggregates indicated that self-assembly of ADF-4 in Sf9 cells is likely to be a nucleated process, which previously has been also suggested for the silk spinning process of *Bombyx mori* (20).

Figure 3:
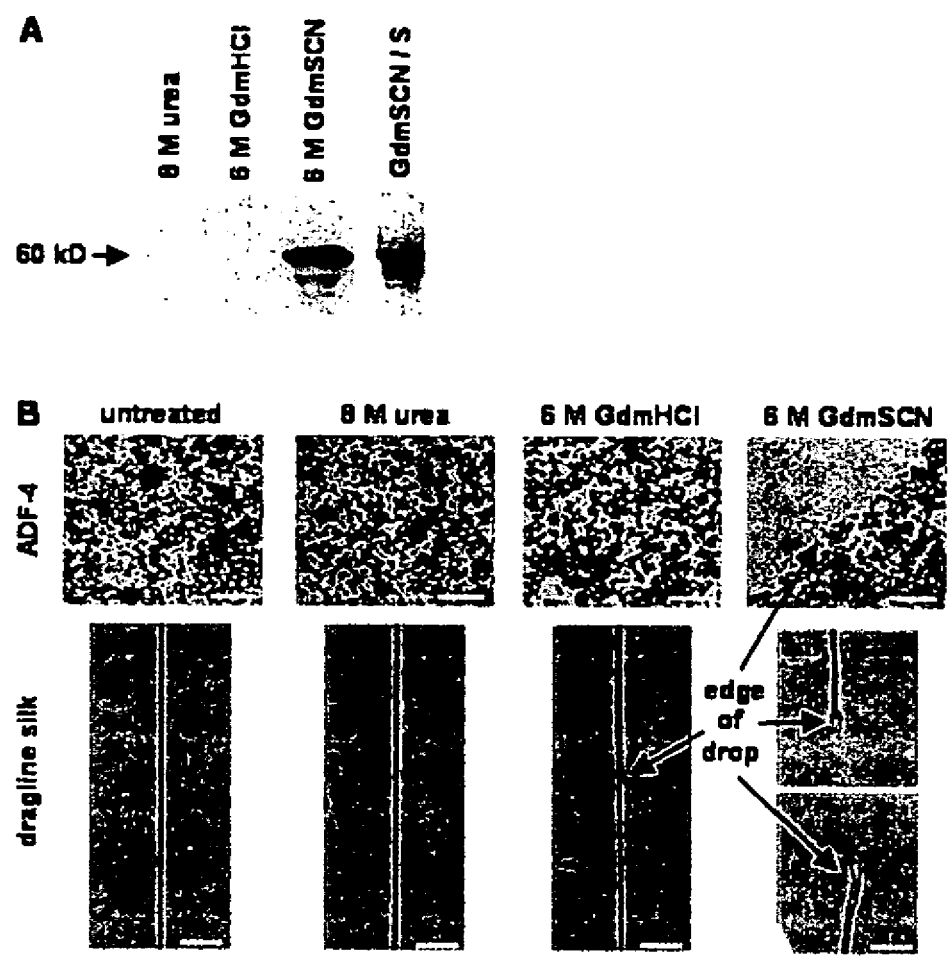
FIG. 3 Chemical stability of ADF-4 filaments and of dragline silk threads. (A) ADF-4 filaments were denatured as indicated. Undissolved filaments and aggregates did not enter the gel. Dissolved ADF-4 was detected by immunoblotting using an anti-His$_6$ antibody. Samples treated with 6M GdmSCN were also silver stained (GdmSCN/S). (B) Air dried ADF-4 filaments on mica and dragline silk threads on polypropylene were incubated for 30 seconds with ~0.1 µl of each solution as indicated. After rinsing with water samples were examined by light microscopy. Scale bar 25 µm.

The size of the filaments formed in the Sf9 cells seemed to be constrained by the volume of the cells making them too short for mechanical force measurements typically performed with silk threads (21). However, the inventors were able to analyze the chemical stability of wet and dry ADF-4 filaments in comparison to natural dragline silk threads of *A. diadematus*. Dragline threads have been reported to be insoluble in many denaturing agents (22). Application of 2% sodium dodecylsulfate (SDS) and 8 M urea apparently had no effect on the structure of ADF-4 filaments and dragline threads after 30 s of exposure (FIG. 3 and data not shown). Immersion of the filaments in 6 M guanidinium chloride (GdmCl) did not lead to solubilization of either ADF-4 filaments or dragline threads, although it did lead to swelling of dragline silk. Such swelling is likely caused by fibre supercontraction (21) which has previously been described for spider silks immersed in aqueous solutions and which results from reformation of hydrogen bonds in the amorphous matrix (21). In contrast to the denaturants mentioned above, a small drop of 6 M GdmSCN completely dissolved ADF-4 filaments as well as dragline threads within seconds (FIG. 3). In consequence the inventors conclude that both structures share molecular interactions, which are responsible for chemical resistance to specific denaturants.

Methods

Plasmid Construction.

The partial cDNAs of adf-3 and adf-4 (gi|1263286; gi|1263288 in pBluescriptSK+) were kindly provided by John Gosline (Vancouver, Canada). The cDNAs were cloned into pFastBac™ donor plasmids from Invitrogen. Sequences coding for peptide tags were provided 5'-terminal to the gene fragments. For His$_6$-tagged proteins, genes were excised from the host vector using SpeI/XhoI and ligated with equally digested pFastBac™HTa. For T7-taged (23) proteins, genes were first cloned into pET21 from Novagen using XhoI and EcoRI. The insert including the T7-Tag coding region was then excised with BglII and XhoI and ligated with pFastBac™1 digested with BamHI/XhoI. For co-expressing adf-3 and adf-4, both genes were cloned into pFasBac™DUAL and provided with sequences coding for T7- and S-Tags (24). The adf-4 gene was excised from pET21-adf-4 with BglII/XhoI and ligated with pFasBac™DUAL cleaved with NheI/BamHI. Two synthetic oligonucleotides (MWG Biotech) were annealed to provide an S-Tag coding sequence, which resulted in double stranded DNA with NheI/BamHI-compatible single strand extensions:

(SEQ ID NO: 5)
5'-CTAGCCCGGGATGAAAGAAACCGCTGCTGCTAAATTCGAACGCCAGC

ACATGGACAGCGGTCGG-3'

(SEQ ID NO: 6)
5'-GATCCCGACCGCTGTCCATGTGCTGGCGTTCGAATTTAGCAGCAGCG

GTTTCTTTCATCCCGGG-3' pET21-adf-3 was digested with NheI/BamHI to remove the T7-Tag coding region. The vector was then ligated with the S-tag encoding DNA. The S-tagged adf-3 was cloned into pFasBac™DUAL-adf-4 using XhoI/XmaI. In the dual construct, adf-3 and adf-4 were under the control of the independent p10 (25) and Polyhedrin (26) promoters. The sequence coding for the secretion signal of Honeybee melittin was amplified by PCR using the pMIB/V5-HisA vector (Invitrogen) as template and the following primers containing CpoI restriction sites:

5'-CCTTCC<u>CGGTCCG</u>CCATGAAATTCTTAGTCAAC (SEQ ID NO: 7)
5'-CCTTCC<u>CGGACCG</u>GGCATAGATGTAAGAAAT (SEQ ID NO: 8)

The resulting PCR product was cut with CpoI and ligated into pFastBac™HTa-adf-4 digested likewise. Positive clones were checked for orientation and correctness by sequencing.

Cell Culture

Sf9 (*Spodoptera frugiperda*; ATCC#: CRL-1711) cells were propagated at 27° C. in BIOINSECT-1 serum-free insect cell culture medium (Biological Industries). Sf9 cells were grown either as monolayers on cover slips in 6 well plates or in shaker flasks agitated at 80 rpm.

Production of Recombinant adf-3 and adf-4 Containing Baculovirus

Competent *E. coli* DH10BAC cells, containing bacmid (baculovirus shuttle vector plasmid) and a helper plasmid, were used to generate recombinant bacmids according to the manufacturer's protocol (Invitrogen). Insertion of the gene into the bacmid was verified by PCR. Sf9 cells were transfected with recombinant bacmid DNA using ESCORT transfection reagent (Sigma-Aldrich) in 6-well plates. The cells were incubated for 5 h at 27° C., rinsed, and incubated for another 72 h. Media were harvested, centrifuged, and the virus-containing supernatant was tittered by plaque assays.

Expression of adf-3 and adf-4

Sf9 cells (3×10$^6$ cells/ml) were infected with the recombinant viruses at various MOIs (multiplicity of infection) ranging from 0.1 to 10. Three days post infection (PI), cells were harvested by centrifugation at 500×g for 5 min.

Detection and Solubility of ADF-3 and ADF-4

Cells were resuspended at 1.2×10$^7$ cells/ml in 100 mM NaCl, 20 mM N-(2-hydroxyethyl)piperazine-N'-(2-ethanesulfonic acid) (HEPES), pH 7.5 and lyzed by sonification. Soluble and insoluble components were separated by centrifugation at 125,000×g for 30 min. For further analysis, pellets were resuspended in 6 M GdmSCN and dialyzed against 8 M Urea. Supernatant and pellet derived from 1.5× 10$^5$ cells were loaded on 10% Tris-Glycine polyacrylamide gels under reducing conditions and blotted onto PVDF membranes (Millipore). Spider silk proteins were detected using a mouse anti-His$_6$ monoclonal antibody (Sigma-Aldrich, 1:10,000) or a mouse anti-T7 monoclonal antibody (Novagen, 1:10,000) and anti-mouse IgG peroxidase conjugate (Sigma-Aldrich, 1:5,000) as secondary antibody. An S-Protein peroxidase conjugate (Novagen, 1:5,000) was used to directly detect S-tagged ADF-3.

Immunocytochemistry

Cells grown on cover slips at 50% confluency were infected with adf-3 or adf-4 containing recombinant viruses at MOI=10. Three days PI cells were fixed with methanol at −20° C. Cover slips were incubated with mouse anti-His$_6$ monoclonal antibody (Roche) at a 1:300 dilution followed by Texas Red conjugated anti-mouse secondary IgG at 1:500 dilution. Cells were observed with an Olympus BX51 fluorescence microscope and images were taken with a Magnafire SP camera or analyzed by confocal microscopy.

ADF-4-thread Purification

Cells were resuspended at 1.2×10$^7$ cells/ml in 100 mM NaCl, 20 mM HEPES, pH 7.5 and lyzed by adding 2% w/v sodium dodecylsulfate followed by incubation at 95° C. for 5 min. Threads were sedimented at 5,000×g followed by washing with 8 M urea and water$_{bidest}$.

Atomic Force (AFM), Scanning Electron (SEM) and Transmission Electron Microscopy (TEM)

Purified filaments were resuspended in water$_{bidest}$ and incubated for 3 min on freshly cleaved mica (AFM) or loaded on Thermanox® plastic cover slips (Nalgene Nunc) (SEM). For AFM, samples were rinsed with water$_{bidest}$ four times and air-dried prior to contact mode imaging using a Multimode SPM (Veeco). For SEM, samples were air dried after removal of the solution, vacuum coated with a gold layer and analyzed with a JSM-5900LV (JEOL Ltd.) at 20 kV. For TEM (JEOL Ltd.) analysis, filaments were adsorbed onto formvar coated grids and negatively stained with uranyl acetate. For immunostaining, fibers were incubated with mouse anti-His$_6$ antibodies followed by labeling with 18 nm gold-conjugated goat anti mouse IgG.

Thread Formation of ADF-4 without His$_6$-tag

To rule out possible influences of the His$_6$-tag on filament formation, T7-tagged ADF-4 was synthesized in Sf9 cells. The filament formation of T7-tagged ADF-4 was apparently indistinguishable to that of His$_6$-tagged ADF-4 (FIG. 4A).

Thread Formation in adf-3 and adf-4 Co-Expressing Cells

In Sf9 cells co-expressing adf-3 and adf-4, filaments could be detected that displayed an apparently indistinguishable morphology in comparison to filaments formed in cells producing only ADF-4 (FIG. 4B).

Expression of adf-3 in Sf9 Cells

Although immunocytochemistry revealed fluorescent foci in adf-3 expressing cells, filament-like structures could not be observed (FIG. 4C,D). Importantly, ADF-3 synthesized in Sf9 cells was largely soluble. Therefore foci formation represented sub-cellular accumulation rather than protein aggregation.

In Vitro Assembly of ADF-4

ADF-4 aggregated upon removal of denaturants by dialysis or after dilution into aqueous buffers. The resulting aggregates did not display any fibrillar morphology (FIG. 4E). Testing chemical stability revealed that in contrast to ADF-4 filaments, formed in the cytosol, the aggregates formed in vitro were soluble in 2% SDS or 8 M Urea (FIG. 4F).

REFERENCES

1. J. M. Gosline, P. A. Guerette, C. S. Ortlepp, K. N. Savage, *J. Exp. Biol.* 202 Pt 23, 3295-3303 (1999).
2. J. Warwicker, *J. Mol. Biol.* 2, 350-362 (1960).
3. A. H. Simmons, E. Ray, L. W. Jelinski, *Macromolecules* 27, 5235-5237 (1994).
4. A. D. Parkhe, S. K. Seeley, K. Gardner, L. Thompson, R. V. Lewis, *J. Mol. Recognit.* 10, 1-6 (1997).
5. J. D. van Beek, S. Hess, F. Vollrath, B. H. Meier, *Proc. Natl. Acad. Sci. U.S.A* 99, 10266-10271 (2002).
6. D. H. Hijirida et al., *Biophys. J.* 71, 3442-3447 (1996).
7. K. Kerkam, C. Viney, D. Kaplan, S. Lombardi, *Nature* 349, 596-598 (1991).
8. D. P. Knight and F. Vollrath, *Proc. R. Soc. Lond.* 519-523 (1999).
9. D. P. Knight and F. Vollrath, *Naturwissenschaften* 88, 179-182 (2001).
10. F. Vollrath, D. Knight, X. W. Hu, *Proc. R. Soc. Lond B Biol. Sci.* 265, 817-820 (1998).
11. E. K. Tillinghast, S. F. Chase, M. A. Townley, *J. Insect Physiol.* 30, 591-596 (1984).
12. D. P. Knight, M. M. Knight, F. Vollrath, *Int. J. Biol. Macromol.* 27, 205-210 (2000).
13. S. Winkler and D. L. Kaplan, *J. Biotechnol.* 74, 85-93 (2000).
14. P. A. Guerette, D. G. Ginzinger, B. H. Weber, J. M. Gosline, *Science* 272, 112-115 (1996).
15. J. Gatesy, C. Hayashi, D. Motriuk, J. Woods, R. Lewis, *Science* 291, 2603-2605 (2001).
16. S. Arcidiacono, C. Mello, D. Kaplan, S. Cheley, H. Bayley, *Appl. Microbiol. Biotechnol.* 49, 31-38 (1998).
17. J. Scheller, K. H. Guhrs, F. Grosse, U. Conrad, *Nat. Biotechnol.* 19, 573-577 (2001).
18. A. Lazaris et al., *Science* 295, 472-476 (2002).
19. V. Vachon, M. J. Paradis, M. Marsolais, J. L. Schwartz, R. Laprade, *Biochemistry* 34, 15157-15164 (1995).
20. G. Li et al., *Eur. J. Biochem.* 268, 6600-6606 (2001).
21. Z. Shao, R. J. Young, F. Vollrath, *Int. J. Biol. Macromol.* 24, 295-300 (1999).
22. S. Lombardi and D. Kaplan, *J. Arachnol.* 18, 297-306 (1990).
23. Kroll, D. J. et al. *DNA Cell Biol.* 12, 441-453 (1993).
24. Kim, J. S. & Raines, R. T. *Protein Sci.* 2, 348-356 (1993).
25. Knebel, D., Lubbert, H. & Doerfler, W. *EMBO J.* 4, 1301-1306 (1985).
26. Smith, G. E., Summers, M. D. & Fraser, M. J. *Mol. Cell. Biol.* 3, 2156-2165 (1983).

What is claimed is:

1. A method of producing spider dragline proteins comprising the following steps:
   a) providing a nucleic acid sequence coding for an *Araneus diadematus* fiber 4 (ADF-4) protein encoded by SEQ ID NO:2 or a variant thereof that differs from the protein encoded by SEQ ID NO:2 by no more than one amino acid substitution, no more than five amino acid deletions, no more than five amino acid insertions, and no more than twenty amino acid additions,
   b) introducing the nucleic acid sequence(s) provided in a) into an insect cell,
   c) expressing the proteins; and
   d) recovering said proteins.

2. The method of claim 1, further comprising providing in step a), a second nucleic acid sequence, coding for an *Araneus diadematus* fiber 3 (ADF-3) protein encoded by SEQ ID NO:1 or a variant thereof that differs from the protein encoded by SEQ ID NO:1 by no more than one amino acid substitution, no more than five amino acid deletions, no more than five amino acid insertions, and no more than twenty amino acid additions.

3. The method of claim 1, wherein the nucleic acid sequence is contained in a vector.

4. The method of claim 3, wherein the vector is an expression vector, which comprises one or more regulatory sequences.

5. The method of claim 4, wherein the regulatory sequences comprise promoter p10 and/or polyhedrin.

6. The method of claim 3, wherein the vector is a viral vector.

7. The method of claim 6, wherein the viral vector is selected from the group consisting of a baculovirus vector system and a vaccinia virus vector system.

8. The method of claim 1, wherein the insect cell is from a lepidopteran insect.

9. The method of claim 8, wherein the insect cell is a Sf9, Sf21 or *Trichoplusia ni* cell.

10. The method of claim 8, wherein the lepidopteran insect is selected from the group consisting of *Spodoptera frugiperda* and *Trichoplusia ni*.

11. The method of claim 1, wherein the only dragline protein expressed is ADF-4 encoded by SEQ ID NO: 2.

12. The method of claim 1, wherein the expression of said protein occurs by secretory or cytoplasmatical expression.

13. A method for producing threads from spider dragline proteins, comprising the following steps: a) expressing the ADF-4 proteins encoded by SEQ ID NO:2 or a variant thereof that differs from the protein encoded by SEQ ID NO:2 by no more than one amino acid substitution, no more than five amino acid deletions, no more than five amino acid insertions, and no more than twenty amino acid additions, b) recovering said proteins, and c) spinning said proteins into threads by a suitable method.

14. The method of claim 13, wherein the only dragline protein is ADF-4 encoded by SEQ ID NO: 2.

15. The method of claim 13, further comprising providing a second nucleic acid sequence, coding for an ADF-3 protein encoded by SEQ ID NO: 1 or a variant thereof that differs from the protein encoded by SEQ ID NO:1 by no more than one amino acid substitution, no more than five amino acid deletions, no more than one amino acid insertions, and no more than twenty amino acid additions, and expressing said ADF-3 protein in step a).

16. A vector, which comprises a nucleic acid sequence coding for an ADF-4 protein encoded by SEQ ID NO:2 or a variant thereof that differs from the protein encoded by SEQ ID NO:2 by no more than one amino acid substitution, no more than five amino acid deletions, no more than five amino acid insertions, and no more than twenty amino acid additions.

17. A baculovirus vector, which comprises a nucleic acid sequence coding for an ADF-4 protein encoded by SEQ ID NO:2 or a variant thereof that differs from the protein encoded by SEQ ID NO:2 by no more than one amino acid substitution, no more than five amino acid deletions, no more than five amino acid insertions, and no more than twenty amino acid additions.

* * * * *